United States Patent [19]

Schwarz et al.

[11] E Patent Number: Re. 32,625

[45] Reissued Date of Patent: Mar. 15, 1988

[54] DYNAMIC TESTING OF ELECTRICAL CONDUCTORS

[75] Inventors: James A. Schwarz, Fayetteville; Robert W. Pasco, Wappingers Falls, both of N.Y.

[73] Assignee: Syracuse University, Syracuse, N.Y.

[21] Appl. No.: 898,032

[22] Filed: Aug. 18, 1986

Related U.S. Patent Documents

Reissue of:

[64] Patent No.: 4,483,629
Issued: Nov. 20, 1984
Appl. No.: 455,852
Filed: Jan. 5, 1983

[51] Int. Cl.[4] ..... G01N 27/14; G01R 27/02

[52] U.S. Cl. ..... 374/57; 324/65 R; 324/158 R

[58] Field of Search ..... 374/45, 46, 44, 57; 324/300, 73 PC; 219/504

[56] References Cited

U.S. PATENT DOCUMENTS

| | | | |
|---|---|---|---|
| 3,266,290 | 8/1966 | Haacke | 374/44 |
| 3,279,239 | 10/1966 | Arends et al. | 374/44 |
| 3,392,324 | 7/1968 | Hermann et al. | 324/73 PC |
| 3,414,811 | 12/1968 | Carter | 374/44 |
| 3,474,530 | 10/1969 | Ainslie et al. | 324/158 R X |
| 3,572,092 | 3/1971 | Zernow | 374/45 |
| 3,958,176 | 5/1976 | Kraeutle | 374/57 X |

FOREIGN PATENT DOCUMENTS

| | | | |
|---|---|---|---|
| 0014069 | 1/1983 | Japan | 324/158 R |

OTHER PUBLICATIONS

"Measurement of Thermal Diffusivity Using a Pyroelectric Detector", C. E. Yeack et al., J. Appl. Phys. 53 6, Jun. 1982, pp. 3947–3949.

"The Effect of Hydrogen Ambient on Electromigration in Al and Al–Cu Thin Films", George Sardo, Syracuse University, 1979.

"Circuit Board Testing", H. E. Meier IBM Tech. Disclosure Bulletin, vol. 23 No. 9, Feb. 1981, 324–73 PC.

*Primary Examiner*—Daniel M. Yasich
*Attorney, Agent, or Firm*—Bruns and Wall

[57] ABSTRACT

A technique is described that permits direct and accurate evaluation of a thin film conductor's reliability which requires only a few hours to carry out. The technique involves a temperature ramp procedure which dynamically exposes a conductor operating under constant current stress to a linear (in time) rise in temperature. Changes in resistivity of the conductor provides kinetic data that is directly related to both the electromigration process and the reliability of the device.

10 Claims, 5 Drawing Figures

DYNAMIC TESTING OF ELECTRICAL CONDUCTORS

Matter enclosed in heavy brackets [ ] appears in the original patent but forms no part of this reissue specification; matter printed in italics indicates the additions made by reissue.

BACKGROUND OF THE INVENTION

This invention relates generally to the mass transport of atoms in a conductor and, in particular, to a process for evaluating the reliability of a thin film interconnector of the type typically used in micro-electronic devices.

As pointed out in U.S. Pat. No. 3,474,530 to Ainslie et al, thin film conductors as typically employed in microcircuits are subjected to a process of electromigration which can under certain conditions lead to early circuit failure. This type of failure generally involves the movement of atoms in the direction of current flow from a first donor region into a second acceptor region. As noted by d'Heurle and Ho in a publication entitled "Thin Films—Interdiffusion and Reactions" published by Wiley-interscience, New York 243–303 (1978), electromigration failure occurs in two separate stages. During the first stage of failure, herein referred to as the electromigration damage (EMD) stage, atoms move out of the donor region under relatively well defined conditions leaving behind voids in the material. The transported atoms are deposited in the acceptor region thereby creating hillocks. The second stage of electromigration failure, which is herein referred to as the catastrophic failure process or (CFP) stage, is characterized by complex temperature and current density variations that lead to a rapid and complete failure of the device.

It is important to note that the two stages of electromigration failure occur in sequence with (EMD) being first in time. The damage that takes place in these early stages of the process proceed under well defined conditions of temperature, temperature distribution, and current density. These conditions remain relatively constant during (EMD) and to a great extent controls the failure process over most of the conductor's life. The second, more dramatic, stage of the failure process, while still an electromigration event, is not characterized by the initial conditions of temperature and current density previously experienced by the conductor but rather by local current densities and temperatures that develop in the now highly stressed donor region. Microscopic defects produced in the conductor by complex temperature and current density variations increase flux divergences in the previously damaged regions thus bringing on rapid, catastrophic and total failure. Although the second stage of failure is a consequence of the first, it nevertheless occurs with rapid kinetics and under less well-defined conditions than those experienced during the earlier stages.

It is important to note that (EMD) occurs over a major portion of the conductor life while (CFP) takes place during a relatively short period at the end of this life span. Accordingly, the physical changes in the conductor which controls the overall failure process typically requires an extremely long period of time to produce catastrophic failure. Heretofore, the kinetics of an electromigration process have been determined by life test experiments known as Mean Time to Failure (MTF) tests. In this type of testing a specimen is generally electrically stressed under isothermal conditions. The kinetics of electromigration are then determined as weighted averages which are taken over a relatively long period of time beginning with the initial stressing of the specimen and ending with failure. As can be seen, these weighted averages are characteristic of both (EMD) and (CFP). The results obtained are therefore of a generally questionable nature in light of the fact that (CFP) depends upon the initial state of the specimen and the specific damage produced during the first stage (EMD) of the process. Testing of many samples is needed to determine (MTF). These tests clearly show that the life span of the specimens can vary by as much as a factor of four. Furthermore, using the test results to determine kinetic parameters relating to the process is also questionable because, as noted, local temperatures and current densities change dramatically during the latter stages of failure and, as a consequence, the time-to-failure values are sometimes more likely to reflect variations in (CFP) rather than (EMD).

Electrical resistance or resistivity measurements have also been used to study the kinetics of the electromigration process. However, like (MTF) measurements, these isothermal resistivity measurements require testing of many samples over long periods of time to determine the kinetic parameters of electromigration. A more thorough treatment of this type of testing is given by Hummel et al, in the Journal of Physics and Chemistry of Solids, Pergamon Press, 1967, Vol. 37, at pp. 73–80, (printed in Great Britain).

SUMMARY OF THE INVENTION

It is therefore an object of the present invention to improve the method and apparatus for evaluating the reliability of a conductor and in particular, a thin film interconnect as typically used in a micro-electronic device.

It is a further object of the present invention to shorten the time required to evaluate the reliability of a conductor.

A still further object of the present invention is to provide for dynamic evaluation of a thin film conductor so that the kinetic parameters controlling failure can be accurately and quickly determined.

Yet another object of the present invention is to accurately predict the life span of a conductor.

Another object of the present invention is to provide a method of characterizing electromigration in a conductor using a temperature ramp technique.

Still another object of the present invention is to solve reliability problems related to large surface-to-volume ratio submicron sized circuit components and the resulting increased material transport rates afforded by high diffusivity paths and short diffusion distances.

While a further object of the present invention is to accurately determine both the activation energy (Q) and pre-exponent (A) values associated with an electromigration process within a relatively short period of time by use of a single experiment.

These and other objects of the present invention are attained by placing a conductive specimen within a controlled ambient and applying a constant current to the specimen while simultaneously therewith heating the specimen at a constant rate. Changes in the specimens resistivity are noted and the activation energy and pre-exponent for the process determined from the observed data. Using a zeroth order relationship for the activated process, the life expectancy of the conductor can also be determined.

BRIEF DESCRIPTION OF THE DRAWINGS

For a better understanding of the present invention reference is had to the following detailed description of the invention which is to be read in conjunction with the associated drawings, wherein.

DESCRIPTION OF THE INVENTION

Figure 1:
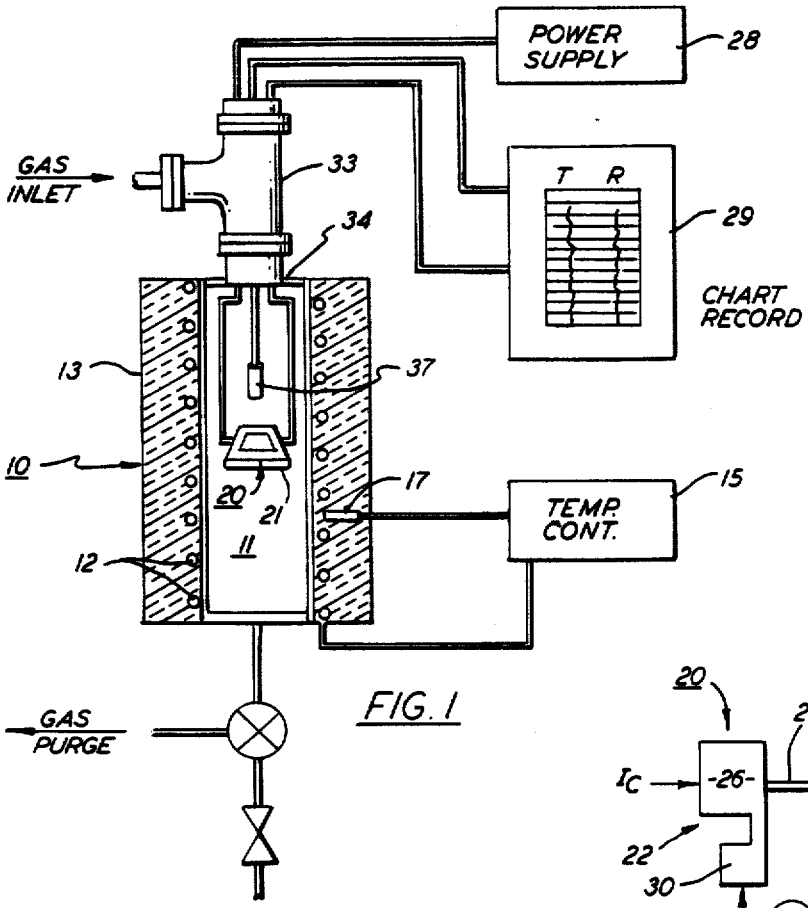
FIG. 1 is a schematic presentation of an apparatus embodying the teachings of the present invention.

The current trend in the electronics industry toward very large scale integration of circuits emphasizes the importance of research concerning the reliability problems associated with submicron sized devices and, in particular, to studying the effects of high material transport rates produced in high diffusity paths having short diffusion distances. One such transport phenomena that leads to shortened conductor life and ultimate circuit failure results from the current induced transport of atoms in the conductor material from a donor region to an acceptor region. This phenomenon is referred to as electromigration and is well known in the semiconductor industry. The kinetic parameters of this type of failure process are the activation energy (Q) and pre-exponential factor (A) for the process.

These parameters are known to be sensitive to both the conductor material and the environment in which it operates. See G. M. Sardo, Masters Thesis, Solid State Science and Technology, Dept. of Chemical Engineering and Materials Science, Syracuse University (1981).

As previously noted, electromigration failure in integrated circuit conductors occurs in two sequential stages. Electromigration damage (EMD) occurs first in time and controls the failure process for a major part of the conductor life. It is therefore fundamentally more important to define or characterize the earlier stages of (EMD) not only because it controls the process but also because it proceeds under clear and well defined conditions of temperature, temperature distribution and current density. It is possible through the measurement of the kinetics of electromigration during the early stages of (EMD) to gain an understanding of the mechanism of the solid state transport phenomena that is associated with the latter failure. As will be explained in greater detail below, this can be accomplished by resistivity measurements.

The kinetics of electromigration have heretofore been determined through Mean Time to Failure (MTF) experiments and are described according to the relationship:

$$(MTF)^{-1} = A'J^n \exp(-Q/kT) = A\exp(-Q/kT) \quad (1)$$

where:

A is the pre-exponential factor for the process;

J is the current density applied to the conductor;

n is an exponent that is generally in the range of $1<n<3$;

Q is the activation energy for the process;

k is Boltzmann's constant; and

T is the process temperature.

The discussion presented by Ho et al in Electro- and Thermo-Transport in Metals and Alloys, TMS-AIME, New York (1977) provides a summary of the application of this equation.

As reported by Hummel, DeHoff and Geier in the Journal of Physics and Chemistry of Solids, Pergamon Press, vol. 37, pp. 73–80 (1976) resistance measurements have been used to study electromigration kinetics. These studies show that the kinetics of the process are well defined only during the early stages of electromigration during which a 5% to 10% relative resistance change takes place. As will be explained in greater detail below, an expression for an activated process similar to the (MTF) expression can be written for resistance measurements. In analogy to equation (1) the following expression for small changes in resistance of a conductor can be written:

$$\frac{1}{R_o}\frac{dR}{dt} = A'^m \exp(-Q/kT) = A\exp(-Q/kT) \quad (2)$$

where:

m is current density exponent determined from resistance change measurements in the range of $1<m<3$;

$R_o$ is the initial resistance of the conductor at room temperature; and dR/dt is the variation in the conductor resistance under (EMD) conditions.

Equation (2) reflects the observed linear time dependence of changes in resistivity as measured during the early stages of electromigration. Deviations from the observed linear behavior at higher resistivity changes and longer time periods cannot be described by a simple kinetic process of integer order. These deviations are likely produced by localized temperature and current density changes due to electromigration damage and signal the onset of catastrophic failure.

Although these and other techniques have been used to study electromigration, none of these techniques are able to supply a dynamic description of the process. It is well known from studies of diffusion in bulk materials that order of magnitude errors can be made by extrapolating high temperature results to lower temperature when changes in the process mechanisms occur. In the present method, resistivity measurements of a conductor are taken through a given temperature range over a predetermined period of time so that the kinetics of (EMD) can be studied dynamically. This method permits systematic investigation of lower temperature process that are normally ignored by isothermal tests. By current stressing a test specimen, such as a thin film conductor, as it is being heated at a uniform linear rate, variations in the electromigration kinetics at the higher temperature can be determined in a relatively short time. These values can then be extrapolated to lower temperatures and the reliability of the device determined.

THEORY

The present method employs a linear temperature ramp to determine the kinetic parameter of an electromigration process. The kinetic parameters, as herein used, refers to the activation energy (Q) and the pre-exponent (A) for the process. As previously noted, in a constant temperature or isothermal electromigration test, the resistance of the conductor is a function of time only so that $R=R(t)$. In the instant process, the process temperature (T) is increased linearly with respect to time so that:

$$T=T_o+\beta t \tag{3}$$

where:

$T_o$ is the initial conductor temperature;

$\beta$ is the heating rate; and t is time.

As can be seen, the conductors resistance now becomes a function of both time and temperature. Assuming Matthiessen's Rule is obeyed (see J. Bass, Advances in Physics, Vol. 21, pg. 431, 1972), it is possible to separate the total resistance of the conductor into two independent additive components:

$$R=R_t[T(t)]+R_{em}[T(t),\ t] \tag{4}$$

where:

$R_T$ is the temperature component;

$R_{em}$ is the electromigration component.

The temperature component is well represented by a linear relationship over the range of interest and therefore:

$$R=R_o[1+\alpha(T-T_o)]+R_{em} \tag{5}$$

where $\alpha$ is the temperature coefficient of resistivity. From equations (3) and (5):

$$R=R_o(1+\alpha\beta t)+R_{em} \tag{6}$$

so that:

$$R_{em}=R-R_o(1+\alpha\beta t)=\Delta R-R_o\alpha\beta t$$
$$R_{em}/R_o=\Delta R/R_o-\alpha\beta t \tag{7}$$

The subscript zero in the above noted equations refers to the initial test conditions at time zero. Stated more concisely, the electromigration component of the relative resistance change is the total relative resistance change minus the linear baseline which consists of the temperature component. The assumption of Matthiessen's Rule that the electromigration component of resistance is independent of the temperature component is implicit in all resistance techniques and is used herein to separate resistance changes due to temperature change from changes due to electromigration.

By subtracting the linear baseline from the total resistance change which can be measured as raw data, the remaining electromigration component of resistivity is related to temperature and time by the zeroth order kinetics for the activated process according to equation (2):

$$(1/R_0)\frac{dR_{em}}{dt}=A\exp(-Q/kT) \tag{8}$$

Noting that $dt=dT/\beta$, and $R_{em}$ at time zero is equal to zero:

$$(1R_0)\int_0^{R_{em}} dR_{em}=(A/B)\int_{T_0}^{T}\exp(-Q/kT)dT \tag{9}$$

The integral in equation (9) appears often in temperature ramp experiments and can be approximated as:

$$(A/B)\int_{T_0}^{T}\exp(-Q/kT)dT= \tag{10}$$
$$(Ak/BQ)\{T^2\exp(-Q/kT)-T_0^2\exp(-Q/kT_0)\}$$

This relationship is valid so long was $Q/2kT>>1$. The second term of equation (10) can be dropped since it is relatively small in comparison to the first term. Combining equations (9) and (10) provides:

$$R_{em}/R_o=\Delta R_{em}/R_o=(Ak/BQ)[T^2\exp(-Q/kT)] \tag{11}$$

and rearranging:

$$T^{-2}(\Delta R_{em}/R_o)=(Ak/\beta Q)\exp(-Q/kT) \tag{12}$$

and taking the logarithm of both sides of equation (12):

$$\ln[T^{-2}(\Delta R_{em}/R_o)]=-Q/kT+\ln(Ak/\beta Q) \tag{13}$$

Figure 3:
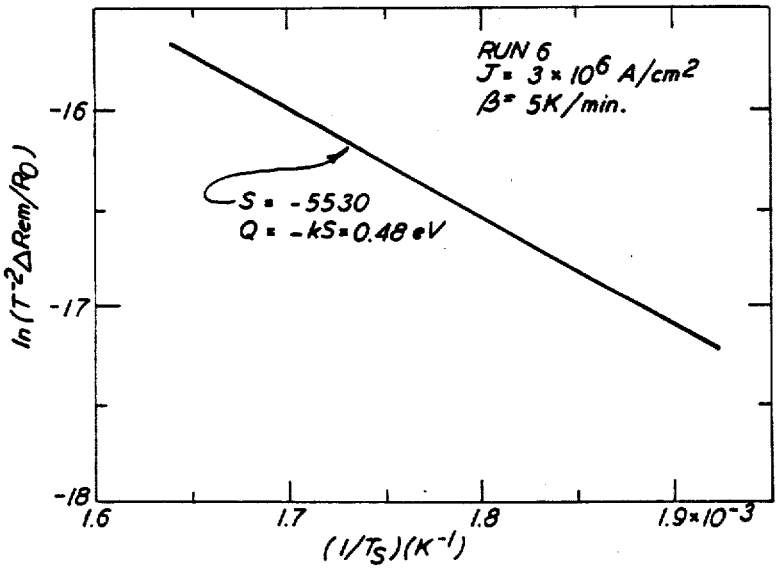
FIG. 3 is a characteristic plot for determining activation energy from data obtained through use of apparatus shown in FIG. 1 wherein an aluminum specimen is stressed at a constant current while being heated at a linear rate.

A characteristic plot of the left hand term in (13) is shown in FIG. 3 and provides a slope (S) and an intercept (I) so that:

$$S=-Q/k \text{ or;}$$
$$Q=-kS \tag{14}$$

where:

$$I=\ln(Ak/\beta Q) \tag{15}$$

so that:

$$A=(\beta Q/k)\exp I=-\beta S\exp I \tag{16}$$

Checking the accuracy of the above approach using calculated data for reasonable values of Q and A, it was determined that the slot shown in FIG. 3 gives accurate determinations of Q values to within 2% or 3%. The pre-exponent values (A), however, were found to be less accurate with errors being in the 10% to 20% range. Accordingly, the (Q) values are first determined using measured resistance values and the characteristic plot as shown in FIG. 3 and the determined (Q) value for the process is then employed to numerically integrate the right hand side of equation (9) to determine the (A) value for each data point. The A values are then averaged to determine the best pre-exponential value for the process.

EXPERIMENTAL

Figure 2:
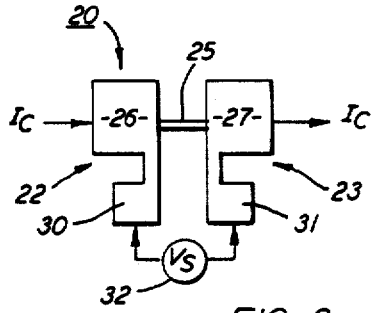
FIG. 2 is an enlarged view of a typical test specimen utilized in the apparatus of FIG. 1.

Turning now to FIGS. 1 and 2, there is shown the apparatus for carrying out the present invention. The apparatus includes an electric furnace 10 that is capable of being accurately controlled so that the temperature of the ambient within the furnace can be increased at a desired linear rate. The furnace includes a test chamber 11 that is wrapped by electrical heating coils 12 and an insulating blanket 13. The heating coils are connected to a suitable temperature control unit 15 and the coil temperature monitored via a thermocouple 17 so as to hold the coils at a desired *temperature* level.

A test specimen 20 is mounted in the chamber 11 upon a support 21 which, in practice, can be a pinned electronic package of the type used in industry to package semiconductive devices and the like. The test specimen is shown in greater detail in FIG. 2. For the purposes of explanation the instant test specimen is a thin film conductor formed from an aluminum film that has been magnetron sputtered onto a 0.8 μm silicondioxide on a silicon wafer. The device further includes two parallelly aligned conductive side members 22 and 23 that are electrically joined by a strip 25 that forms the specimen under test. The side members include a pair of enlarged upper pads 26 and 27 that are connected in series with a power supply 28 (FIG. 1) so that a current is caused to flow through the strip. A second smaller pair of lower pads 30 and 31 are connected to a voltmeter 32 which is situated in recorder 29 (FIG. 1) and used to determine the resistivity of the strip.

A flanged connector 33 is secured in the top wall 34 of the chamber through which the chamber communicates with a source of gas (not shown), the previously noted power supply 28 and the chart recorder 29. The power supply is adapted to apply a constant current to the test specimen throughout the test period. A temperature sensor 37 is positioned within the chamber in close proximity to the specimen and provides a constant stream of ambient temperature information to the recorder. The term ambient, as herein used, shall mean the atmosphere maintained within the chamber which is typically at some pressure that is equal or greater than the atmospheric pressure surrounding the chamber. Related voltage data is also brought out of the chamber through the flanged connector to the recorder. This information is recorded on a strip chart along with the temperature information.

Prior to testing, the specimen is annealed by heating it within the chamber for about four hours in a helium or inert atmosphere. This prevents the specimen from becoming annealed during the test period and thus prevents erroneous measurements from being generated.

The ambient within the chamber is controlled by means of the gas inlet 40 and a gas purge line 41 passing out of the bottom wall of the chamber. Once the specimen has been mounted, the chamber is sealed and an inert or reactive gas is fed into the chamber to totally replace the air atmosphere.

Raw experimental data are in the form $V_s/V_o = R/R_o$ as a function of temperature. The low temperature portion of the resistivity curve is quite linear and represents resistance changes produced by changes in temperature only. Low temperature data is therefore used to determine the temperature coefficient of resistivity. In accordance with equation (7), subtraction yields the electromigration component as a function of temperature. The actual [stripe] *strip* temperature, however, is needed in order to determine the kinetics of the process.

The [stripe] *strip* temperature is higher than the ambient temperature because of the current stressing. The resistance of the [stripe] *strip* as a function of current density is measured over a given temperature range and the average [stripe] *strip* temperature rise above the ambient rise for various current densities is found. This added rise in [stripe] *strip* temperature is constant over the observed range. Using this data measured ambient temperatures are corrected to obtain average [stripe] *strip* temperatures and the data recorded in terms thereof.

FIG. 3 shows the results of a test conducted in the apparatus described above using a conductive test stripe of aluminum having a thickness 0.8 μm, a width of 6.35 μm and a length of 380 μm. The specimen was current stressed at $3\times10^6$ amp/cm$^2$ and the heating rate was held at a constant rate of 5 K.°/min. From previously conducted MTF experiments conducted upon similar aluminum conductors, it was indicated that the activation energy should be about 0.43 eV. As can be seen, the test results showed the value of (Q) to be 0.48 eV which compares quite favorably with the previously indicated results. Similar favorable results were also found for pre-exponential values by integrating the right hand side of equation (9).

The invention will now be explained in greater detail with reference to the following examples:

Example 1

Employing the apparatus illustrated in FIGS. 1 and 2, a pair of identically constructed aluminum test specimens were mounted in the furnace. The first specimen, specimen 1, was exposed to a helium atmosphere during testing while the second specimen, specimen 2, was exposed to a hydrogen atmosphere. Each specimen was stressed at $3\times10^6$ amps/cm$^2$ while being heated to a constant linear rate of 1° K./min from room temperature to about 600° K.

Figure 4:
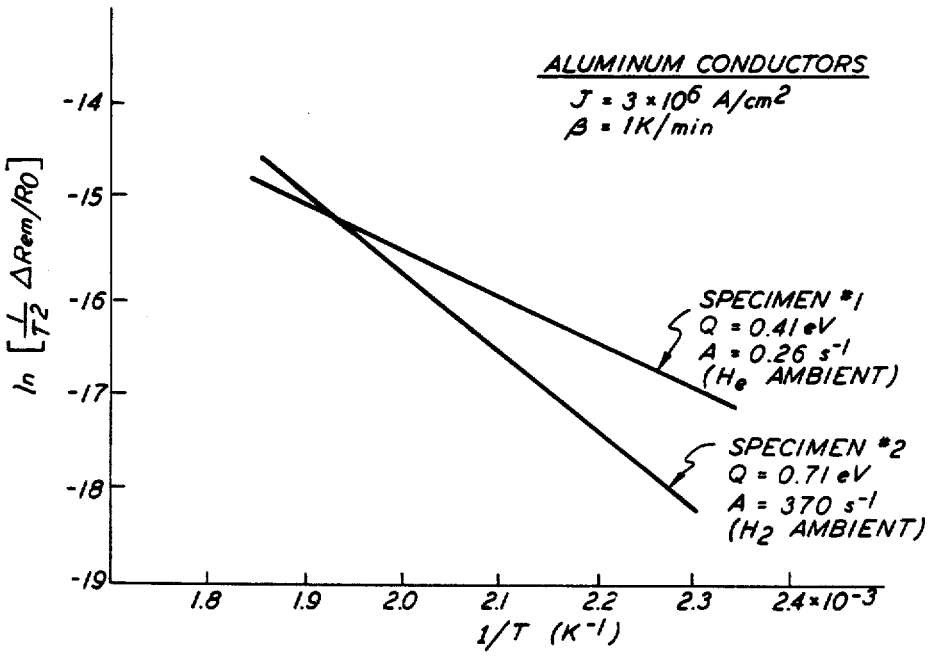
FIG. 4 illustrates characteristic plots similar to the one shown in FIG. 3 for two identical aluminum specimens that have been tested in different ambients while being stressed at the same current and heated at the same rate.

Tests described about were conducted on both specimens in different ambients and characteristic plots, similar to that shown in FIG. 3, for the activated process prepared. These plots are illustrated in FIG. 4. The pre-exponential (A) and activation (Q) values were determined using this data. The values for specimen contained in the helium ambient were:

$$Q=0.41 \text{ eV}$$
$$A=0.265 \text{ s}^{-1}.$$

while the values for the specimen contained in the hydrogen ambient were:

$$Q=0.71 \text{ eV}$$
$$A=370 \text{ s}^{-1}.$$

From the integrated form of equation (2) above, the following relationship can be written:

$$\frac{R_{em}}{R_e} = A\exp(-Q/kT)\Delta t \tag{17}$$

Rearranging equation (17) provides:

$$i = \frac{\Delta R_{em}}{R_e} \frac{1}{A} \exp(Q/kT) \tag{18}$$

Experience has shown that the $\Delta R_{em}/R_o$ factor representing failure has a typical value of between 0.10 and 0.50. An arbitrary value of 0.20 was selected which would be representative based on previously observed resistivity changes. Using the known values in equation (18) and a Boltzmann's constant of $8.617\times10^{-5}$eV/K.° the Δt value for each specimen was calculated for room temperature at two different current densities. The results are tabulated below:

| SPEC NO | ATMO | $J = 3 \times 10^6$ A/cm$^2$ | $J = 5 \times 10^6$ A/cm$^2$ |
|---|---|---|---|
| #1 | He | 76.6 days | 7.6 years* |
| #2 | $H_2$ | 17.5 years | 629 years* |
| | | FOR: $\Delta R_{cm} = 0.20\ Ro$ T = 298° K. | |

*Assuming A $a\ J^2$ (m = 2)

As can be seen from the table above, the specimen contained in the hydrogen atmosphere had a life expectancy that was greater than the specimen contained in the helium atmosphere by a factor of about 83 for specimens stressed at $3 \times 10^6$ amps/cm$^2$.

Example 2

Figure 5:
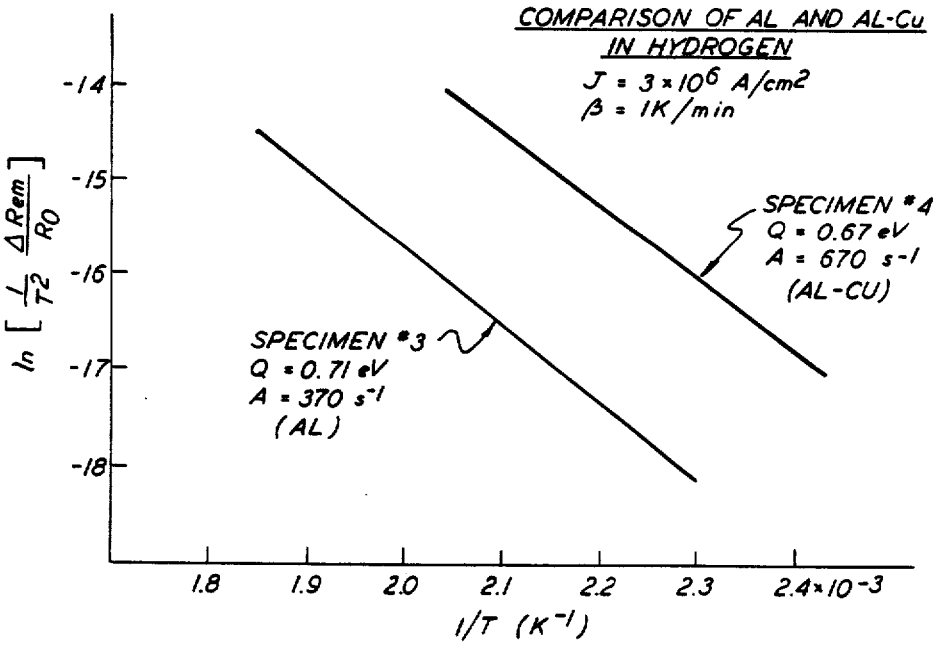
FIG. 5 also illustrates characteristic plots similar to the one shown in FIG. 3 for two specimens that are formed of different materials that have been stressed in the same ambient at the same current heated at the same rate.

Two new specimens were constructed as noted above from two different materials. One specimen, specimen 3, was constructed of aluminum while the other specimen, specimen 4, was constructed of aluminum containing about 2% copper. Again using the above described apparatus and procedures of the present invention, each specimen was tested in a hydrogen atmosphere while being stresses at $3 \times 10^6$ A/cm$^2$. The temperature of each specimen was increased at a linear rate of 1° K./min. The characteristic plots of the two activated processes are illustrated in FIG. 5. As explained in reference to Example 1, the data was used to find the life expectancy of each specimen and the results are tabulated below:

| SPEC NO | MATL | $J = 3 \times 10^6$ A/cm$^2$ | $J = 5 \times 10^6$ A/cm$^2$ |
|---|---|---|---|
| #3 | Al | 17.5 years | 629 years* |
| #4 | Al—CU | 2.0 years | 73.2 years* |
| | | FOR: $\Delta R_{cm} = 0.20\ Ro$ T = 298° K. | |

*Assuming A $a\ J^2$ (m = 2)

From the results of Example 2 it can be seen that the life expectancy and/or reliability of a pure aluminum conductor is considerably greater than that of one alloyed with copper when operating at room temperature in a hydrogen environment.

These results clearly show that detailed information concerning a given conductor can be obtained in one experiment using the method and apparatus of the present invention. While this invention has been described with reference to the structure disclosed herein, it is not necessarily confined to the details as set forth in the application and the invention is intended to cover any modifications or changes that might come within the scope of the following claims.

We claim:

1. A method for determining the kinetic parameters of activation energy and pre-exponential factor which characterizes electromigration failure in a thin film conductor that is subject to high current densities at elevated temperatures, said method [includes] *including* the steps of placing a thin film conductor in a [predetermined atmosphere] *testing device*, electrically stressing the thin film conductor, while in said [atmosphere] *testing device*, by applying a uniform current thereto, heating the stressed conductor to increase the conductor temperature at a linear rate with respect to time, measuring changes in resistance of the current stressed conductor as it is being heated at a linear rate, reducing the measured changes in resistance by those changes due to the temperature dependent components of resistance to determine the changes in resistance produced by the electromigration failure process, determining the activation energy and pre-exponential factor by relating the measured changes in resistance with respect to time produced by the electromigration failure process to the following zeroth order rate expression:

$$1/R_o\ dR/dt = A \exp(-Q/kT)$$

where: $R_o$ is the initial resistance of the thin film conductor, dR/dt is the variation in the conductor resistance produced by the electromigration process, Q is the activation energy for the process, A is the pre-exponential for the process, k is Boltzmann's constant and T is absolute temperature.

2. The method of claim 1 that further includes the step of annealing the [unstressed] conductor prior to heating the said conductor at a linear rate.

3. The method of claim 1 including the further step of determining the activation energy for the electromigration process by plotting:

$$\ln [T^{-2}(\Delta R_{em}/R_o)] \text{vs } 1/T$$

where: $\Delta R_{em}$ is the change in resistance of the conductor produced by the electromigration process.

4. The method of claim 3 wherein the activation energy of the process is determined from the plot according to the relationship $$Q = -ks$$

where: s is the slope of the plotted line.

5. The method of claim 3 that includes the further step of determining the pre-exponential factor from the relationship:

$$A = -\beta s \exp I$$

where: $\beta$ is the heating rate, and I is the intercept of the plotted line.

6. The method of claim 5 that includes the further step of determining the life expectancy of the conductor by the relationship:

$$t = \frac{\Delta R_{em}}{R_e} \frac{l}{A} \exp(Q/KT)$$

where: t is time in seconds.

7. Apparatus for testing a thin film conductor to determine the kinetic parameters of activation energy and pre-exponential factor which lead to electromigration failure in the conductor that includes

[a hermetically sealed chamber having] means to support a thin film conductor [in said chamber],

[means to maintain a controlled atmosphere within the chamber]

heating means to increase [the temperature of the atmosphere within the chamber] at a linear rate

[whereby] the temperature of the conductor [is also heated at a linear rate], electrical means for maintaining a constant current flow through the conductor as [is] *the letter* is being heated *by said heating means* at said linear rate, first means to measure the changes in resistance of the conductor as the temperature thereof is changed *by said heating means* at a linear rate over a preselected given period of time, and said means to measure the change in temperature of the [atmosphere within the chamber] *thin film conductor* whereby the increase changes in the conductor resistance due to the electromigration failure process can be determined by relating said changes to an activation energy and pre-exponential factor, wherein a record of the changes in resistance over said given time period [time] is obtained.

8. The apparatus of claim 7 which further includes a recording means operatively connected to said first and second means for providing the record of the changes in resistance and temperature over the given *time* period [of time.]

9. The apparatus of claim 7 wherein [the] *said means to support the thin film conductor includes a hermetically sealed chamber, and* means to control the chamber atmosphere [further] *which* includes valve means for regulating pressure of the atmosphere within the chamber.

10. The apparatus of claim 7 wherein said heating means includes an electrical heater [that is wrapped about the outside of the chamber].

* * * * *

UNITED STATES PATENT AND TRADEMARK OFFICE

CERTIFICATE OF CORRECTION

PATENT NO. : Re. 32,625

DATED : March 15, 1988

INVENTOR(S) : JAMES A. SCHWARZ, ROBERT W. PASCO

It is certified that error appears in the above-identified patent and that said Letters Patent is hereby corrected as shown below:

Column 10, line 55 " $\frac{\Delta R_{em}}{R_e}$ " should read -- $\frac{\Delta R_{em}}{R_o}$ -- .

Column 11, line 4, "letter" should read --latter--;

line 11, "said" should read --second--.

Signed and Sealed this

Sixth Day of December, 1988

*Attest:*

DONALD J. QUIGG

*Attesting Officer*

*Commissioner of Patents and Trademarks*